United States Patent
Kim et al.

(10) Patent No.: US 12,318,390 B2
(45) Date of Patent: *Jun. 3, 2025

(54) PHARMACEUTICAL COMPOSITION FOR ORAL ADMINISTRATION COMPRISING AMINOPYRIMIDINE DERIVATIVE OR ITS SALT

(71) Applicant: YUHAN CORPORATION, Seoul (KR)

(72) Inventors: Seongkyu Kim, Seoul (KR); Deokkyu Lee, Seoul (KR); Soo-Won Kim, Gyeonggi-do (KR); Jun-Mo Yang, Gyeonggi-do (KR); Yoong-Sik Park, Seoul (KR)

(73) Assignee: Yuhan Corporation, Seoul (KR)

( * ) Notice: Subject to any disclaimer, the term of this patent is extended or adjusted under 35 U.S.C. 154(b) by 731 days.

This patent is subject to a terminal disclaimer.

(21) Appl. No.: 17/285,161

(22) PCT Filed: Oct. 17, 2019

(86) PCT No.: PCT/IB2019/058862
§ 371 (c)(1),
(2) Date: Apr. 14, 2021

(87) PCT Pub. No.: WO2020/079637
PCT Pub. Date: Apr. 23, 2020

(65) Prior Publication Data
US 2021/0322428 A1    Oct. 21, 2021

(30) Foreign Application Priority Data
Oct. 18, 2018 (KR) .................. 10-2018-0124171

(51) Int. Cl.
*A61K 31/5377*    (2006.01)
*A61K 9/00*    (2006.01)
*A61K 9/20*    (2006.01)

(52) U.S. Cl.
CPC ........ *A61K 31/5377* (2013.01); *A61K 9/0053* (2013.01); *A61K 9/2013* (2013.01); *A61K 9/2018* (2013.01); *A61K 9/2027* (2013.01); *A61K 9/2054* (2013.01); *A61K 9/2059* (2013.01)

(58) Field of Classification Search
CPC .............. A61K 31/5377; A61K 9/0053; A61K 9/2013; A61K 9/2018; A61K 9/2027; A61K 9/2054; A61K 9/2059
See application file for complete search history.

(56) References Cited

U.S. PATENT DOCUMENTS

| | | | |
|---|---|---|---|
| 6,517,871 | B1 | 2/2003 | Venkatesh et al. |
| 9,539,098 | B2 * | 1/2017 | Suh ................ A61F 2/3603 |
| 11,453,646 | B2 * | 9/2022 | Oh ................ G01N 33/5008 |
| 2008/0131505 | A1 * | 6/2008 | Li ................ A61K 9/1682 |
| | | | 264/109 |
| 2015/0190374 | A1 | 7/2015 | Boersen et al. |
| 2016/0102076 | A1 | 4/2016 | Suh et al. |
| 2018/0153899 | A1 | 6/2018 | David et al. |
| 2019/0031619 | A1 | 1/2019 | Boersen et al. |
| 2019/0111057 | A1 | 4/2019 | Finnie et al. |
| 2020/0289472 | A1 | 9/2020 | Charo et al. |
| 2021/0322323 | A1 * | 10/2021 | Maximilien ............ A61P 35/00 |

FOREIGN PATENT DOCUMENTS

| | | |
|---|---|---|
| CN | 1315853 A | 10/2001 |
| CN | 101528201 A | 9/2009 |
| CN | 104788427 A | 7/2015 |
| CN | 106795144 A | 5/2017 |
| JP | 2006-524635 A | 11/2006 |
| JP | 2014-533733 A | 12/2014 |
| JP | 2017-501201 A | 1/2017 |
| JP | 2017-537954 A | 12/2017 |
| JP | 2018-515566 A | 6/2018 |
| JP | 2019-510832 A | 4/2019 |
| WO | 2013/082003 A1 | 6/2013 |
| WO | 2016/060443 A2 | 4/2016 |
| WO | 2017/061621 A1 | 4/2017 |
| WO | 2017/176965 A1 | 10/2017 |
| WO | WO-2018194356 A1 * | 10/2018 ......... A61K 31/5377 |

OTHER PUBLICATIONS

Kazemi P, et al. Drug Design, Development and Therapy. 2017;11:241-251. (Year: 2017).*
Shanmugam, S. BioImpacts: BI. 2015;5(1):55-63.) (Year: 2015).*
Anonymous: "Study Record Versions History of Changes for Study: NCT03556436 Clinical Trial to Evaluate the Safety and Effects of Ethnicity and Food on Pharmacokinetics of YH25448", Sep. 6, 2018, pp. 1-10.

* cited by examiner

*Primary Examiner* — Joseph K McKane
*Assistant Examiner* — Quincy McKoy
(74) *Attorney, Agent, or Firm* — BakerHostetler

(57) ABSTRACT

The present disclosure provides a pharmaceutical composition for oral administration comprising: N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or its pharmaceutically acceptable salt as an active ingredient; and a combination of microcrystalline cellulose and mannitol as a diluent.

18 Claims, 10 Drawing Sheets

PHARMACEUTICAL COMPOSITION FOR ORAL ADMINISTRATION COMPRISING AMINOPYRIMIDINE DERIVATIVE OR ITS SALT

CROSS-REFERENCE TO RELATED APPLICATIONS

The present application is the National Stage of International Patent Application No. PCT/IB2019/058862 filed Oct. 17, 2019, which claims priority to Korean Application No. 10-2018-0124171, filed Oct. 18, 2018, the entire contents of both of which are incorporated herein by reference.

TECHNICAL FIELD

The present disclosure relates to a pharmaceutical composition for oral administration comprising an aminopyrimidine derivative or its salt. More particularly, the present disclosure relates to a pharmaceutical composition comprising N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or its salt and a combination of microcrystalline cellulose and mannitol as a diluent.

BACKGROUND

WO 2016/060443 discloses an aminopyrimidine derivative, for example, N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or its pharmaceutically acceptable salt. Lazertinib or its pharmaceutically acceptable salt has activity of selectively inhibiting protein kinase, particularly, protein kinase for a mutant epidermal growth factor receptor, and may provide, for example, an effective and safe treatment method for non-small cell lung cancer. Lazertinib or its pharmaceutically acceptable salt has been known as irreversible EGFR TKI which has less effect on wild-type EGFR, strong inhibitory activity on T790M single active mutation (EGFRm) and double mutation, and excellent selectivity, and is expected to exhibit a therapeutically effective effect in the treatment of patients with primary cancer of progressive non-small cell lung cancer and progressive non-small cell lung cancer accompanied by brain metastasis.

When Lazertinib or its salt is formulated as a composition for oral administration, it may be considered to formulate Lazertinib or its salt in the form of an immediate-release pharmaceutical composition having a mechanism in which the active ingredient is immediately released in the stomach and then transferred to the small intestine to be absorbed. In the formulation of such an immediate-release pharmaceutical composition, it is required to minimize the effect of pH changes in the stomach, for example, according to foods or simultaneous-administered drugs (e.g., an antacid, etc.). For example, since pH in the empty stomach is not constant ranging from pH 1 to pH 3.5 and also an average pH in a postprandial stomach is pH 4 (pH 3 to 5), deviations in dissolution rate may occur depending on the physicochemical properties of an active ingredient, which may result in changes in absorption rate and bioavailability.

SUMMARY

The present inventors found that when N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or its salt is formulated using a combination of specific diluents, it is possible to prepare an immediate-release pharmaceutical composition capable of minimizing the effect according to changes in pH environment in the stomach. Further, the present inventors found that the pharmaceutical composition may be formulated to secure excellent stability and exhibit significantly increased bioavailability.

Therefore, an object of the present disclosure is to provide a pharmaceutical composition for oral administration of Lazertinib or its pharmaceutically acceptable salt comprising a combination of specific diluents.

According to an aspect of the present disclosure, there is provided a pharmaceutical composition for oral administration comprising N-(5-(4-(4-((dimethylamino)methyl)-3-phenyl-1H-pyrazol-1-yl)pirimidine-2-ylamino)-4-methoxy-2-morpholinophenyl)acrylamide or its pharmaceutically acceptable salt as an active ingredient; and a combination of microcrystalline cellulose and mannitol as a diluent.

In the pharmaceutical composition of the present disclosure, a weight ratio of the microcrystalline cellulose to the mannitol may be in the range of 1:0.9 to 1:3 and preferably 1:0.9 to 1.1.5.

The pharmaceutical composition of the present disclosure may further include croscarmellose sodium as a disintegrating agent, and the croscarmellose sodium may exist in a range of 0.5 to 10 wt %, preferably 2 to 5 wt %, with respect to the total weight of the composition. Further, the pharmaceutical composition of the present disclosure may further include magnesium stearate as a lubricant. In one embodiment, the pharmaceutical composition of the present disclosure includes N-(5-(4-(4-((dimethylamino)methyl)-3-phenyl-1H-pyrazol-1-yl)pirimidine-2-ylamino)-4-methoxy-2-morpholinophenyl)acrylamide or its pharmaceutically acceptable salt as an active ingredient; a combination of microcrystalline cellulose and mannitol as a diluent; croscarmellose sodium as a disintegrating agent; and magnesium stearate as a lubricant.

In the pharmaceutical composition of the present disclosure, the active ingredient may be N-(5-(4-(4-((dimethylamino)methyl)-3-phenyl-1H-pyrazol-1-yl)pirimidine-2-ylamino)-4-methoxy-2-morpholinophenyl)acrylamide mesylate.

In one embodiment, N-(5-(4-(4-((dimethylamino)methyl)-3-phenyl-1H-pyrazol-1-yl)pirimidine-2-ylamino)-4-methoxy-2-morpholinophenyl)acrylamide mesylate may be a crystalline form having a PXRD pattern with peaks at 5.614, 12.394, 14.086, 17.143, 18.020, 19.104, 21.585, 22.131, and 22.487° 2θ±0.2° 2θ. In another embodiment, N-(5-(4-(4-((dimethylamino)methyl)-3-phenyl-1H-pyrazol-1-yl)pirimidine-2-ylamino)-4-methoxy-2-morpholinophenyl)acrylamide mesylate may be a crystalline form having a differential scanning calorimeter (DSC) thermogram with anendothermic peak at 210 to 230° C., preferably, 217±2° C.

According to the present disclosure, it was found that when N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or its salt is formulated using a combination of specific diluents, that is, a combination of microcrystalline cellulose and mannitol, it is possible to prepare an immediate-release pharmaceutical composition capable of minimizing the effect according to changes in pH environment in the stomach. Further, the pharmaceutical composition of the present disclosure may be formulated to secure excellent stability and may achieve significantly increased bioavailability.

DETAILED DESCRIPTION OF EXEMPLARY EMBODIMENTS

Figure 1:
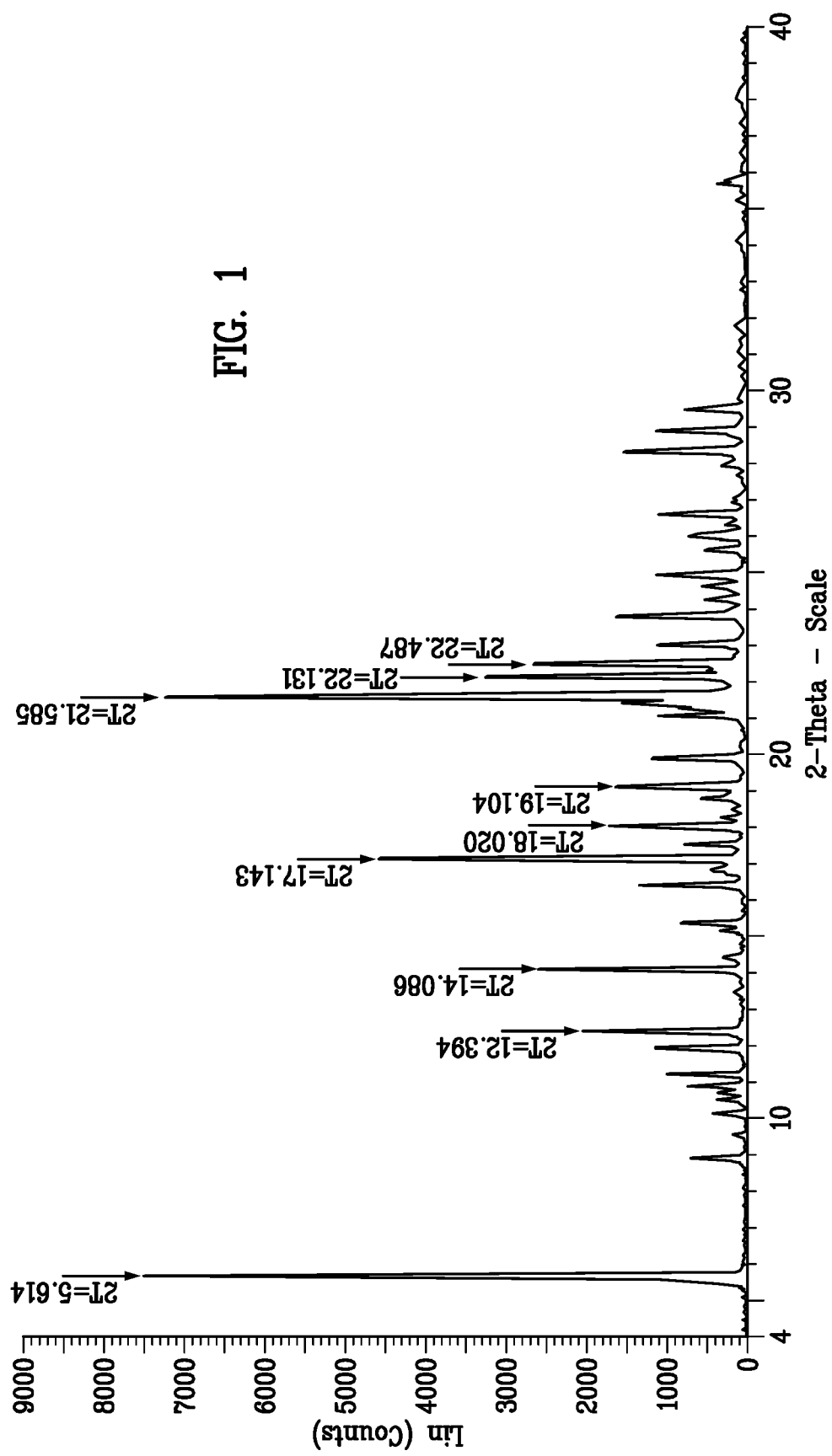
FIG. 1 is a graph of powder X-ray diffractometry (PXRD) of Lazertinib mesylate prepared in Reference Example 1.

The present disclosure provides a pharmaceutical composition for oral administration comprising N-(5-(4-(4-((dimethylamino)methyl)-3-phenyl-1H-pyrazol-1-yl)pirimidine-2-ylamino)-4-methoxy-2-morpholinophenyl) acrylamide (Lazertinib) or its pharmaceutically acceptable salt as an active ingredient; and a combination of microcrystalline cellulose and mannitol as a diluent.

In this specification, the 'diluent' and the 'additive' have the same meaning and may be used interchangeably. According to the present disclosure, it was found that when Lazertinib or its salt is formulated using a combination of specific diluents, that is, a combination of microcrystalline cellulose and mannitol, it is possible to prepare an immediate-release pharmaceutical composition capable of minimizing the effect according to changes in pH environment in the stomach. The changes in pH environment in the stomach include a pH change by diet; and a pH change by drugs, for example, a proton pump inhibitor such as esomeprazole or a H2-receptor antagonist such as cimetidine, an antacid, and the like, but is not limited thereto.

In the pharmaceutical composition of the present disclosure, N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) or its pharmaceutically acceptable salt may be used in therapeutically effective amounts. For example, Lazertinib or its pharmaceutically acceptable salt may be used in a range of 10 to 320 mg as Lazertinib per unit formulation (e.g., per unit tablet), and may be used in amounts of, for example, 10 mg, 20 mg, 40 mg, 80 mg, 100 mg, 120 mg, 160 mg, 240 mg, or 320 mg.

The pharmaceutical composition of the present disclosure includes a combination of specific diluents, that is, a combination of microcrystalline cellulose and mannitol. According to the present disclosure, it is found that when the weight ratio of mannitol with respect to microcrystalline cellulose is 0.5 times to three times, Lazertinib or its salt may minimize the effect according to changes in pH environment in the stomach. Accordingly, the weight ratio of microcrystalline cellulose to mannitol may be in a range of preferably 1:0.5 to 1:3, more preferably 1:0.9 to 1:3, much more preferably 1:0.9 to 1:1.5, and particularly preferably about 1:0.95 to 1:1.2.

The pharmaceutical composition of the present disclosure may include a disintegrating agent and/or a lubricant (or a glidant), in addition to the diluent.

The disintegrating agent may be a conventional disintegrating agent used in the field of pharmaceutics. However, according to the present disclosure, it is found that in the case of using a specific disintegrating agent, that is, croscarmellose sodium among various disintegrating agents, the precipitation is significantly delayed when the drug disintegrated/dissolved in the stomach is transferred to the intestine. Accordingly, it is preferred that the pharmaceutical composition of the present disclosure includes croscarmellose sodium as a disintegrating agent. The croscarmellose sodium may exist, for example, in a range of 0.5 to 10 wt %, preferably 2 to 5 wt %, with respect to the total weight of the composition.

The lubricant (or the glidant) may be a conventional lubricant used in the field of pharmaceutics. However, according to the present disclosure, it is found that a specific lubricant, that is, magnesium stearate among various lubricants has particularly excellent compatibility with Lazertinib or its salt, thereby securing excellent stability. Accordingly, it is preferred that the pharmaceutical composition of the present disclosure includes magnesium stearate as a lubricant (or the glidant). The magnesium stearate may be used in a sufficient amount to achieve a sufficient lubricating effect, and for example, may exist in a range of 0.4 to 2 wt %, with respect to the total weight of the composition, but is not limited thereto.

In one embodiment, the pharmaceutical composition of the present disclosure includes N-(5-(4-(4-((dimethylamino) methyl)-3-phenyl-1H-pyrazol-1-yl)pirimidine-2-ylamino)-4-methoxy-2-morpholinophenyl)acrylamide or its pharmaceutically acceptable salt as an active ingredient; a combination of microcrystalline cellulose and mannitol as a diluent; croscarmellose sodium as a disintegrating agent; and magnesium stearate as a lubricant.

It was found that Lazertinib mesylate is excellent in stability, solubility, and bioavailability compared to the compound in the form of free-base and may be prepared with high purity. Further, it was found that there is an advantage that Lazertinib mesylate has excellent bioavailability even in the case of co-administration with e.g., an antacid, as well as in the case of administration thereof alone. Accordingly, in the pharmaceutical composition of the present disclosure, the active ingredient may be Lazertinib mesylate. In one embodiment, the pharmaceutical composition of the present disclosure may consist of 5 to 54 wt % of Lazertinib mesylate; 45 to 87 wt % of a combination of microcrystalline cellulose and mannitol; 0.5 to 10 wt % of croscarmellose sodium; and 0.4 to 2 wt % of magnesium stearate. In another embodiment, the pharmaceutical composition of the present disclosure may consist of 7 to 46 wt % of Lazertinib mesylate; 50 to 87 wt % of a combination of microcrystalline cellulose and mannitol; 2 to 5 wt % of croscarmellose sodium; and 0.5 to 1.5 wt % of magnesium stearate.

Lazertinib mesylate may be a crystalline form. In one embodiment, Lazertinib mesylate may be a crystalline form having a PXRD pattern with peaks at 5.614, 12.394, 14.086, 17.143, 18.020, 19.104, 21.585, 22.131, and 22.487° 2θ±0.2° 2θ. In another embodiment, Lazertinib mesylate may be a crystalline form having a differential scanning calorimeter (DSC) thermogram with an endothermic peak at 210 to 230° C., preferably 217±2° C. Lazertinib mesylate may have an onset of 214±2° C.

The Lazertinib mesylate may be prepared by a preparation method comprising (a) mixing Lazertinib free-base with a single organic solvent or a mixed solvent, followed by adding methane sulfonic acid thereto to form Lazertinib mesylate, and (b) crystallizing Lazertinib mesylate by adding an organic solvent to the mixture of step (a).

The single organic solvent of step (a) is not particularly limited, but may be selected from the group consisting of acetone, methyl ethyl ketone, and ethyl acetate. The mixed solvent of step (a) may be a mixed solvent of water and one or more suitable organic solvents. Specifically, a mixed solvent of water and one or more organic solvents selected from acetone and methyl ethyl ketone is preferable, but is not limited thereto. A mixing ratio of the water and the organic solvent may be 1:1 to 1:10 in volume ratio and specifically 1:4 to 1:6, but is not limited thereto. The step (a) may be performed at a temperature of 20 to 70° C., preferably 45 to 60° C.

The crystallizing of step (b) may be performed by adding the organic solvent to the mixture obtained in step (a), stirring, cooling, and filtering the mixture, and then drying it to obtain the resulting solid. The organic solvent of step (b) may be the same as or different from the single organic solvent of step (a). Specifically, the organic solvent in step (b) may be at least one selected from the group consisting of acetone, methyl ethyl ketone, and ethyl acetate. The organic solvent in step (b) may be added in volume of 3 mL to 20 mL per 1 g of Lazertinib free-base used in step (a). Specifically, the organic solvent may be added in volume of 5 mL to 20 mL per 1 g of Lazertinib free-base used in step (a) and, more specifically, in volume of 5 mL to 10 mL, but is not limited thereto. The mixture obtained by addition of the organic solvent may be cooled to a temperature of 0 to 30° C., preferably 0 to 10° C., and then dried at a temperature of 30 to 70° C. to isolate Lazertinib mesylate.

The pharmaceutical composition of the present disclosure may be used for preventing or treating allograft rejection, graft-versus-host disease, diabetic retinopathy, choroidal angiogenesis due to age-related visual loss, psoriasis, arthritis, osteoarthritis, rheumatoid arthritis, pannus invasion of synovial membrane in arthritis, multiple sclerosis, myasthenia gravis, diabetes mellitus, diabetic vascular disease, retinopathy of prematurity, infantile hemangioma, non-small cell lung cancer, bladder cancer, head and neck cancer, prostate cancer, breast cancer, ovarian cancer, gastric cancer, pancreatic cancer, psoriasis, fibrosis, atherosclerosis, recurrent stenosis, autoimmune disease, allergy, respiratory disease, asthma, transplant rejection, inflammation, thrombosis, retinal conduit proliferation, inflammatory bowel disease, Crohn's disease, ulcerative colitis, bone disease, graft or bone marrow transplant rejection, lupus, chronic pancreatitis, cachexia, septic shock, fibrosis and differentiating skin diseases or disorders, central nervous system diseases, neurodegenerative diseases, Alzheimer's disease, Parkinson's disease, disorders or symptoms associated with nerve damage following brain or spinal cord injury and exon metamorphosis, acute or chronic cancer, ocular disease, viral infection, heart disease, lung disease or kidney disease, and bronchitis. The pharmaceutical composition of the present disclosure may be used for the prevention or treatment of preferably acute or chronic cancer, more preferably lung cancer, most preferably non-small cell lung cancer or brain metastatic non-small cell lung cancer, but is not limited thereto.

Hereinafter, the present disclosure will be described in more detail through Examples and Test Examples. However, these Examples and Test Examples are just illustrative to the present disclosure, and the present disclosure is not limited to these Examples and Test Examples.

In the following Examples and Test Examples, "Lazertinib" refers to N-(5-(4-(4-((dimethylamino)methyl)-3-phenyl-1H-pyrazol-1-yl)pirimidine-2-ylamino)-4-methoxy-2-morpholinophenyl)acrylamide, and "Lazertinib mesylate" refers to mesylic acid salt of N-(5-(4-(4-((dimethylamino)methyl)-3-phenyl-1H-pyrazol-1-yl)pirimidine-2-ylamino)-4-methoxy-2-morpholinophenyl)acrylamide.

Reference Example 1: Preparation of Lazertinib Mesylate

A compound prepared in the same manner as the method disclosed in WO 2016/060443, i.e., N-(5-(4-(4-((dimethylamino)methyl)-3-phenyl-1H-pyrazol-1-yl)pirimidine-2-ylamino)-4-methoxy-2-morpholinophenyl)acrylamide (Lazertinib) (1,100.0 g, 1,983.2 mmol), acetone (4.4 L), and purified water (1.1 L) were put into a reactor and heated to 45 to 55° C. under stirring. Methane sulfonic acid (186.8 g, 1,943.6 mmol) was diluted in purified water (0.55 L) and then the resulting solution was added thereto while maintaining a temperature of 45° C. or higher. The resulting mixture was stirred for 30 minutes or more to prepare a mixture containing mesylic acid salt of N-(5-(4-(4-((dimethylamino)methyl)-3-phenyl-1H-pyrazol-1-yl)pirimidine-2-ylamino)-4-methoxy-2-morpholinophenyl)acrylamide.

Thereafter, in order to crystallize the mesylate compound in the mixture, acetone (8.8 L) was added thereto, while maintaining a temperature of 40 to 50° C. The resulting mixture was stirred for 30 minutes or more, cooled to 0 to 5° C., and then stirred for 3 hours or more. The reaction mixture is filtered under the reduced pressure, a wet cake was washed with acetone (5.5 L), and then the resulting solid was dried at 55° C. in vacuum to obtain 1,095.8 g of Lazertinib mesylate (yield: 84.9%).

Results of measuring the obtained Lazertinib mesylate by $^1$H-NMR (400 MHz, DMSO-$d_6$) are as follows.

$^1$H-NMR (400 MHz, DMSO-$d_6$) δ 9.79 (s, 1H), 9.35 (s, 1H), 9.21 (s, 1H), 8.78 (s, 1H), 8.59 (d, 1H), 8.33 (s, 1H), 7.77 (d, 2H), 7.55 (m, 3H), 7.34 (d, 1H), 6.94 (s, 1H), 6.71-6.76 (q, 1H), 6.28-6.31 (d, 1H), 5.81-5.83 (d, 1H), 4.48 (s, 2H), 3.90 (s, 3H), 3.81-3.83 (t, 4H), 2.86-2.88 (t, 4H), 2.66 (s, 6H), 2.35 (s, 3H).

As a result of measuring PXRD of the obtained Lazertinib mesylate, a PXRD pattern with peaks at 5.614, 12.394, 14.086, 17.143, 18.020, 19.104, 21.585, 22.131, and 22.487° 2θ±0.2° 2θ was shown (FIG. 1). The PXRD spectrum was measured using Bruker D8 advance (X-ray source: CuKα, tube voltage: 40 kV/tube current: 40 mA, emission slit: 0.3, and scattering slit: 0.3).

Figure 2:
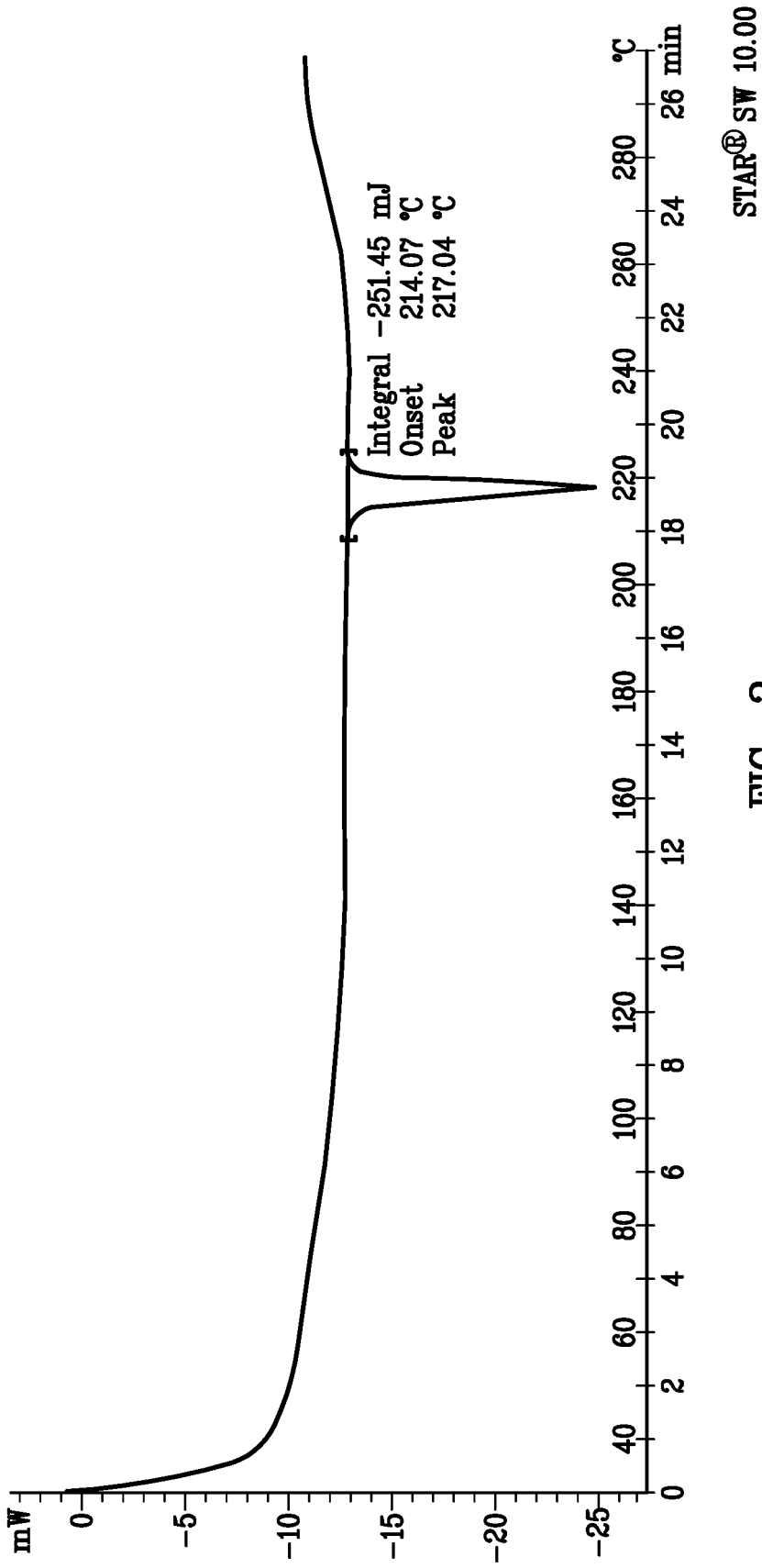
FIG. 2 is a graph of differential scanning calorimeter (DSC) of Lazertinib mesylate prepared in Reference Example 1.

As a result of measuring the obtained Lazertinib mesylate by DSC, an endothermic peak was shown at about 217° C. in a DSC graph (FIG. 2). The DSC was measured using Mettler Toledo DSC 1 STAR (sample container: sealed aluminum pan, 99% nitrogen condition, and raised to 10° C. per minute from 30° C. to 300° C.).

Reference Example 2: Property Evaluation and Pharmacokinetic Test of Lazertinib Mesylate (1) Solubility Test The solubility according to pH and the solubility in artificial gastric juice, artificial intestinal fluid, water and ethanol were compared with each other with respect to Lazertinib mesylate and Lazertinib free-base.

120 mg of Lazertinib mesylate (100 mg as Lazertinib) prepared in Reference Example 1 was added to 5 mL of a buffer solution having each pH disclosed in the following Table 1, artificial gastric juice, artificial intestinal fluid, water, or ethanol and then stirred under conditions of 37° C., water bath, and 50 rpm for 12 hours. In addition, 100 mg of Lazertinib free-base (prepared in the same manner as the method described in WO 2016/060443) was tested under the same conditions. After 12 hours of stirring, the concentration of the dissolved Lazertinib was measured and the solubility was compared. The results were shown in Table 1 below.

TABLE 1

| | Solubility (mg/mL) | | | | | | | | | | |
|---|---|---|---|---|---|---|---|---|---|---|---|
| | pH 1.2 | pH 2.0 | pH 3.0 | pH 4.0 | pH 5.0 | pH 6.0 | pH 7.0 | Artificial gastric juice (FaSSGF) | Artificial intestinal fluid (FaSSIF) | water | Ethanol |
| Lazertinib free-base | 4.4 | 3.7 | 1.9 | 1.0 | 0.01 | 0.003 | 0.001 | 1.5 | 0.027 | 0.001 | 0.599 |
| Lazertinib mesylate | 14.9 | 14.1 | 17.9 | 20.9 | 18.4 | 1.2 | 0.018 | 10.1 | 0.68 | 21.6 | 17.3 |

As illustrated in Table 1, Lazertinib mesylate had solubility in water 20,000 times higher than that of Lazertinib free-base, solubility in artificial gastric juice (FaSSGF) about 10 times higher than that of Lazertinib free-base, and solubility in artificial intestinal fluid (FaSSIF) about 25 times higher than that of Lazertinib free-base.

(2) Stability Test

A stability test for Lazertinib mesylate was performed under a stressed condition and an accelerated condition, and each condition was as shown in Table 2 below.

TABLE 2

| Classification | Stressed condition | Accelerated condition |
|---|---|---|
| Temperature | 60 ± 2° C. | 40 ± 2° C. |
| Humidity | 75 ± 5% (relative humidity) | 75 ± 5% (relative humidity) |
| Container | 10 mL glass vial and rubber lid | polyethylene double bag, High Density Polyethylene (HDPE) Bottle |
| Sampling time | At start, after 2 weeks, and after 4 weeks | At start, after 1 month, after 3 months, and after 6 months |

(2-1) Stability Test Under Stressed Condition

Figure 3:
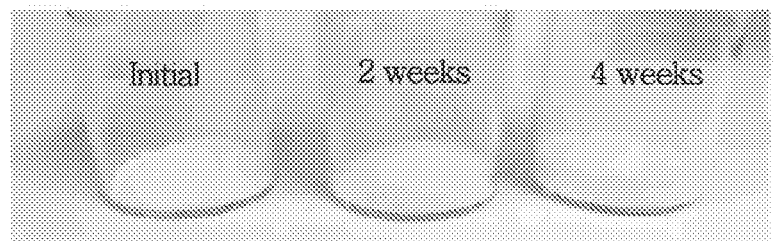
FIG. 3 is a photograph illustrating results of the stability test performed under a stressed condition with respect to Lazertinib mesylate prepared in Reference Example 1 (Initial: at start, 2 weeks: after 2 weeks, 4 weeks: after 4 weeks).

Stability for Lazertinib mesylate was tested under the stressed conditions described in Table 2 above, and the results were illustrated in FIG. 3 and Tables 3 and 4 below. The measurement conditions for PXRD and DSC are the same as described in Reference Example 1.

TABLE 3

| PXRD pattern | | | DSC Onset (° C.) | | | Appearance (color) | | |
|---|---|---|---|---|---|---|---|---|
| Start | 2 weeks | 4 weeks | Start | 2 weeks | 4 weeks | Start | 2 weeks | 4 weeks |
| — | Same pattern | Same pattern | 214 | 214 | 214 | White | White | White |

Further, the measurement results of high performance liquid chromatography (HPLC) were shown in Table 4 below, and the measurement conditions were as follows. Mobile phase buffer: 250 mM of ammonium acetate in water (Mobile phase A: buffer/water/acetonitrile, Mobile phase B: acetonitrile, Column: Xbridge BEH C18 XP)

TABLE 4

| Purity (%) | | | | Content (%) | | | | Water Content (%) | | | |
|---|---|---|---|---|---|---|---|---|---|---|---|
| Start | 2 weeks | 4 weeks | Variation | Start | 2 weeks | 4 weeks | Variation | Start | 2 weeks | 4 weeks | Variation |
| 99.2 | 99.3 | 99.3 | +0.1 | 98.8 | 97.7 | 98.9 | +0.1 | 2.48 | 2.71 | 2.70 | +0.22 |

(2-2) Stability Test Under Accelerated Condition

Figure 4:
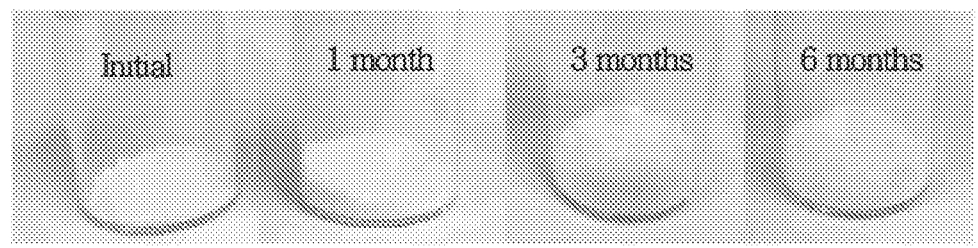
FIG. 4 is a photograph illustrating results of the stability test performed under an accelerated condition with respect to Lazertinib mesylate prepared in Reference Example 1 (Initial: at start, 1 month: after 1 month, 3 months: after 3 months, 6 months: after 6 months).

Stability for Lazertinib mesylate was tested under the accelerated conditions described in Table 2 above, and the results were illustrated in FIG. 4 and Tables 5 and 6 below. The measurement conditions for PXRD and DSC are the same as described in Example 1.

TABLE 5

| PXRD pattern | | | | DSC Onset (° C.) | | | | Appearance (color) | | | |
|---|---|---|---|---|---|---|---|---|---|---|---|
| Start | 1 month | 3 months | 6 months | Start | 1 month | 3 months | 6 months | Start | 1 month | 3 months | 6 months |
| — | Same pattern | Same pattern | Same pattern | 214 | 214 | 214 | 214 | White | White | White | White |

Further, the measurement results of high performance liquid chromatography (HPLC) were shown in Table 6 below, and measurement conditions were the same as disclosed in (2-2).

TABLE 6

| Purity (%) | | | | | Content (%) | | | | | Water Content (%) | | | | |
|---|---|---|---|---|---|---|---|---|---|---|---|---|---|---|
| Start | 1 month | 3 months | 6 months | Variation | Start | 1 month | 3 months | 6 months | Variation | Start | 1 month | 3 months | 6 months | Variation |
| 99.2 | 99.3 | 99.3 | 99.3 | +0.1 | 98.8 | 98.9 | 98.9 | 99.1 | +0.3 | 2.48 | 2.73 | 3.19 | 3.01 | +0.53 |

From the results of the stability test, Lazertinib mesylate showed a slight change in purity and water content between at the start point and at the end point of the stability test, showed no change in the PXRD pattern, and showed no change in appearance observed by a color, and thus the stability thereof was excellent.

(3) Comparative Pharmacokinetic Test for Lazertinib Mesylate and Lazertinib Free-Base in Normal Rats and Esomeprazole-Treated Rats With respect to Lazertinib mesylate and Lazertinib free-base, pharmacokinetics was compared with each other in normal rats and rats treated with esomeprazole which was a proton pump inhibitor, respectively. Specifically, in the normal rats and the esomeprazole-treated rats, maximum blood concentrations ($C_{max}$) and areas under the blood concentration curve ($AUC_{last}$) were compared with each other, respectively, to evaluate the absorption of drugs in animals.

In order to perform the comparative pharmacokinetic test, about 250 g of 8-week-old male rats (SD rat) were selected as test animals, and Lazertinib mesylate and Lazertinib free-base were suspended in 0.5% methyl cellulose, and then orally administered to normal rats in a dose of 30 mg/5 mL/kg.

Figure 5:
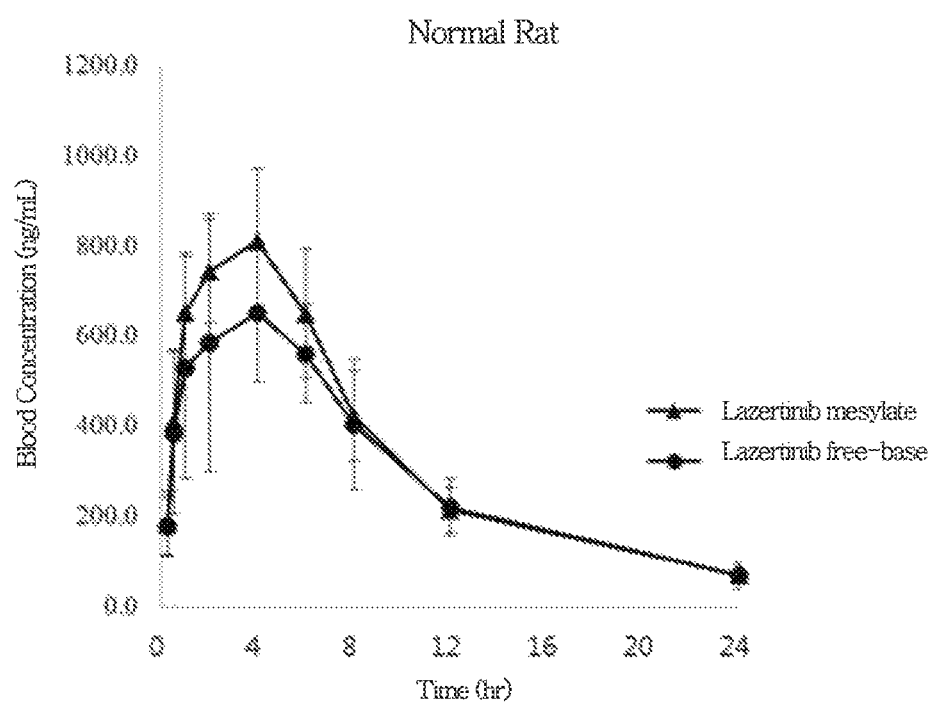
FIG. 5 illustrates results of the comparative pharmacokinetic test for Lazertinib mesylate and Lazertinib free-base, which is performed in normal rats.
Figure 6:
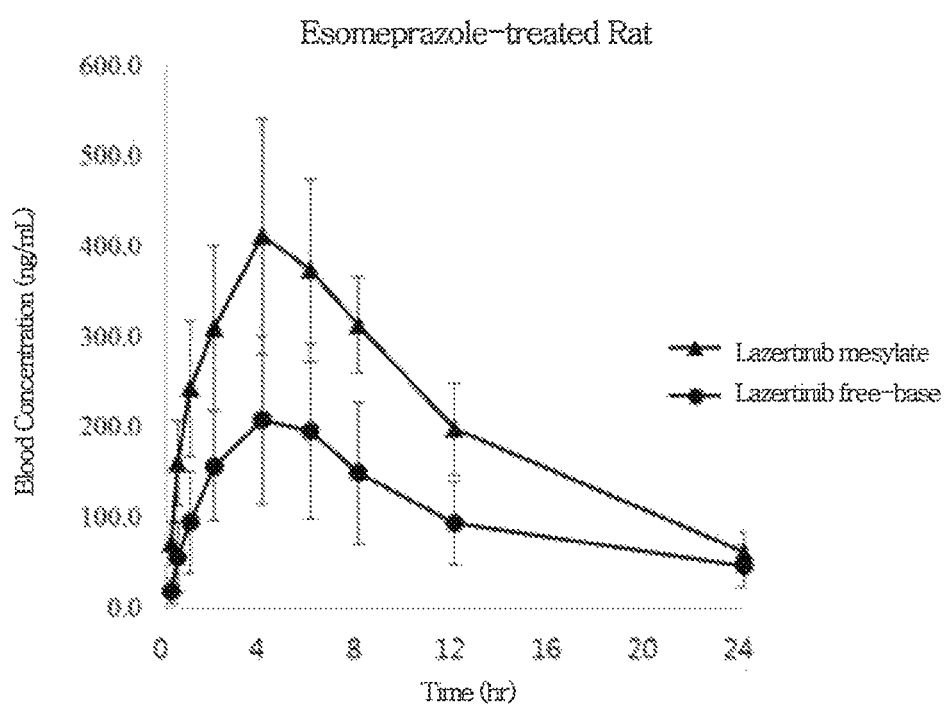
FIG. 6 illustrates results of the comparative pharmacokinetic test for Lazertinib mesylate and Lazertinib free-base, which is performed in esomeprazole-treated rats.

Further, esomeprazole (esomeprazole magnesium dihydrate, manufactured from Sigma-Aldrich) was intravenously administered to about 250 g of 8-week-old male rats in a dose of 5 mg/2 mL/kg for 3 days, and then Lazertinib mesylate and Lazertinib free-base were orally administered in the same dose (30 mg/5 mL/kg) as the dose administered to the normal rats. The results (the maximum blood concentration and the area under the blood concentration curve) of the comparative pharmacokinetic test obtained therefrom were shown in Table 7 and FIGS. 5 and 6.

TABLE 7

| Pharmacokinetic parameter | Normal rat | | Esomeprazole-treated rat | |
|---|---|---|---|---|
| | Lazertinib mesylate | Lazertinib free-base | Lazertinib mesylate | Lazertinib free-base |
| Maximum blood concentration ($C_{max}$, ng/mL) | 815.6 | 725.7 | 427.5 | 223.0 |
| Area under the blood concentration curve ($AUC_{last}$, ng · hr/mL) | 8139.0 | 7293.6 | 5210.9 | 2636.7 |

As shown in the above results, in the case of Lazertinib free-base, the maximum blood concentration and the area under the blood concentration curve were observed with 11.0% and 10.4% lower than Lazertinib mesylate in the normal rats, respectively, and the maximum blood concentration and the area under the blood concentration curve were observed with 47.8% and 49.4% lower than Lazertinib mesylate in the esomeprazole-treated rats, respectively. That is, it can be seen that Lazertinib free-base has a lower body exposure than Lazertinib mesylate.

Further, in the esomeprazole-treated rats, in the case of Lazertinib mesylate, the maximum blood concentration and the area under the blood concentration curve were reduced by 47.6% and 36.0%, compared with the normal rats, respectively. However, in the case of Lazertinib free-base, the maximum blood concentration and the area under the blood concentration curve were reduced by 69.3% and 63.8%, compared with the normal rats, respectively. From these results, it can be seen that Lazertinib mesylate shows a less change in pharmacokinetic according to the esomeprazole administration than Lazertinib free-base, thereby maintaining a high blood concentration in rats.

Figure 7:
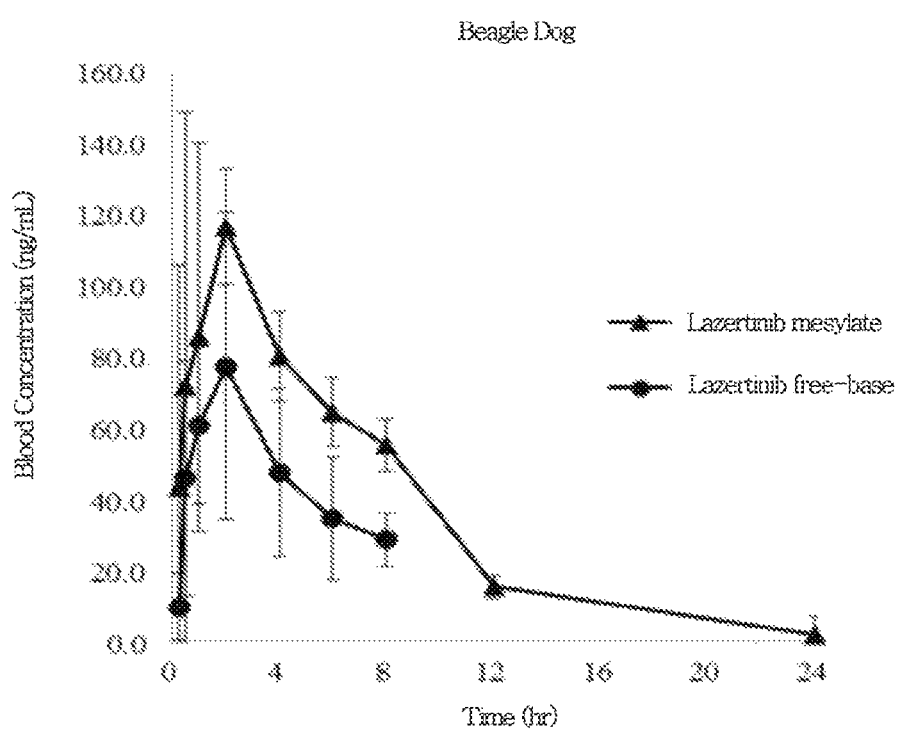
FIG. 7 illustrates results of the comparative pharmacokinetic test for Lazertinib mesylate and Lazertinib free-base, which is performed in beagle dogs.

(4) Pharmacokinetic Test for Lazertinib Mesylate and Lazertinib Free-Base in Beagle Dogs In order to perform a comparative pharmacokinetic test, about 10 kg of 15 to 17-month-old male beagle dogs were selected as test animals, and Lazertinib mesylate and Lazertinib free-base were suspended in 0.5% methyl cellulose, and then orally administered to a beagle dog in a dose of 5 mg/2 mL/kg. The results (the maximum blood concentration and the area under the blood concentration curve) of the comparative pharmacokinetic test obtained therefrom were shown in Table 8 and FIG. 7.

TABLE 8

| | Lazertinib mesylate | Lazertinib free-base |
|---|---|---|
| Maximum blood concentration ($C_{max}$, ng/mL) | 134.7 | 80.7 |
| Area under the blood concentration curve ($AUC_{last}$, ng · hr/mL) | 811.5 | 379.1 |

As shown in the above results, as a tested result for the beagle dog, it was observed that Lazertinib free-base showed the maximum blood concentration and the area under the blood concentration curve which were 40.1% and 50.4% lower than Lazertinib mesylate, respectively. From these results, it can be seen that Lazertinib mesylate maintains a higher blood concentration than Lazertinib free-base in the beagle dog.

As such, Lazertinib mesylate is excellent in solubility and bioavailability, compared to Lazertinib free-base. Lazertinib mesylate has improved stability, solubility and bioavailability, and is excellent in terms of its high purity.

Examples 1 to 8. Preparation of Tablet

According to the ingredients and contents of Table 9 below, a tablet containing Lazertinib mesylate was prepared. The content in Table 9 represents mg per unit tablet. Specifically, an active ingredient, an additive, and a disintegrating agent were mixed using a blender, and then a lubricant was additionally mixed. The resulting mixture was compressed using a tablet press machine (XP1 from Corsch Corporation) to prepare a tablet.

TABLE 9

| | | Examples (mg/tablet) | | | | | | | |
|---|---|---|---|---|---|---|---|---|---|
| Ingredient | | 1 | 2 | 3 | 4 | 5 | 6 | 7 | 8 |
| Active ingredient | Lazertinib mesylate | 11.73 | 11.73 | 23.47 | 23.47 | 46.93 | 46.93 | 93.86 | 93.86 |
| | (as Lazertinib) | (10.00) | (10.00) | (20.00) | (20.00) | (40.00) | (40.00) | (80.00) | (80.00) |
| Additive | Microcrystalline cellulose | 65.27 | 42.55 | 67.53 | 35.38 | 65.07 | 32.52 | 67.14 | 33.29 |
| | D-mannitol | 65.00 | 87.72 | 66.00 | 98.15 | 65.00 | 97.55 | 66.00 | 99.85 |
| Disintegrating agent | croscarmellose sodium | 6.00 | 6.00 | 6.00 | 6.00 | 6.00 | 6.00 | 6.00 | 6.00 |
| lubricant | magnesium stearate | 2.00 | 2.00 | 2.00 | 2.00 | 2.00 | 2.00 | 2.00 | 2.00 |
| Total weight | | 150.00 | 150.00 | 165.00 | 165.00 | 185.00 | 185.00 | 235.00 | 235.00 |

Examples 9 to 13. Preparation of Tablet

According to the ingredients and contents of Table 10 below, a tablet containing Lazertinib mesylate was prepared. The content in Table 10 represents mg per unit tablet. Specifically, an active ingredient, an additive, and a disintegrating agent were mixed using a blender, and then a lubricant was additionally mixed. The resulting mixture was compressed using a tablet press machine (XP1 from Corsch Corporation) to prepare a tablet.

TABLE 10

| | | Examples (mg/tablet) | | | | |
|---|---|---|---|---|---|---|
| Ingredient | | 9 | 10 | 11 | 12 | 13 |
| Active ingredient | Lazertinib mesylate (as Lazertinib) | 117.33 (100.00) | 140.79 (120.00) | 187.72 (160.00) | 281.58 (240.00) | 375.44 (320.00) |
| Additive | Microcrystalline cellulose | 67.67 | 100.71 | 134.28 | 201.42 | 268.56 |
| | D-mannitol | 67.00 | 99.00 | 132.00 | 198.00 | 264.00 |
| Disintegrating agent | croscarmellose sodium | 6.00 | 9.00 | 12.00 | 18.00 | 24.00 |
| Lubricant | magnesium stearate | 2.00 | 3.00 | 4.00 | 6.00 | 8.00 |
| Total weight | | 260.00 | 352.50 | 470.00 | 705.00 | 940.00 |

Comparative Examples 1 to 6. Preparation of Tablet

According to the ingredients and contents of Table 11 below, a tablet containing Lazertinib mesylate was prepared. The content in Table 11 represents mg per unit tablet. Specifically, an active ingredient, an additive, and a disintegrating agent were mixed using a blender, and then a lubricant was additionally mixed. The resulting mixture was compressed using a tablet press machine (XP1 from Corsch Corporation) to prepare a tablet.

TABLE 11

| | | Comparative Examples (mg/tablet) | | | | | |
|---|---|---|---|---|---|---|---|
| Ingredient | | 1 | 2 | 3 | 4 | 5 | 6 |
| Active ingredient | Lazertinib mesylate (as Lazertinib) | 46.93 (40.00) | 93.86 (80.00) | 11.73 (10.00) | 11.73 (10.00) | 93.86 (80.00) | 93.86 (80.00) |
| Additive | Microcrystalline cellulose | 35.07 | 36.14 | — | — | — | — |
| | lactose hydrate | 95.00 | 97.00 | — | — | — | — |
| | Microcrystalline cellulose | — | — | 98.00 | — | 67.14 | 67.14 |
| | D-mannitol | — | — | 32.27 | — | 66.00 | 66.00 |
| | Microshellac* | — | — | — | 130.27 | — | — |
| Disintegrating agent | croscarmellose sodium | 6.00 | 6.00 | 6.00 | 6.00 | — | — |
| | Crospovidone | — | — | — | — | 6.00 | — |
| | sodium starch-glycolate | — | — | — | — | — | 6.00 |
| Lubricant | magnesium stearate | 2.00 | 2.00 | 2.00 | 2.00 | 2.00 | 2.00 |
| Total weight | | 185.00 | 235.00 | 150.00 | 150.00 | 235.00 | 235.00 |

*Microshellac: Additive consisting of 73 to 77 % of lactose hydrate and 23 to 27 % of microcrystalline cellulose Test Example 1. Compatibility Test with Lazertinib Mesylate and/Lubricant/Glidant A mixture (Mixture A) of 1,000 mg of Lazertinib mesylate and 1,000 mg of magnesium stearate, a mixture (Mixture B) of 1,000 mg of Lazertinib mesylate and 1,000 mg of sodium stearyl fumarate, and a mixture (Mixture C) of 1,000 mg of Lazertinib mesylate and 1,000 mg of colloidal silicon dioxide (i.e., Aerosil 200) were compressed by applying pressure of 1 kN, respectively, to prepare a compression material. The contents of a maximum unknown impurity and a total impurity in the mixture before compression and the contents of a maximum unknown impurity and a total impurity in the obtained compression material were measured, respectively. And also, the obtained compression material were put into a HDPE-made glass bottle and stored under a severe condition (60±2° C., 75±5% RH) for 1 week, and then contents of the maximum unknown impurity and the total impurity were measured. The content of the impurity was analyzed by ultra performance liquid chromatography (UPLC) under the following conditions.

<ULPC Conditions>
  Column: ACQUITY UPLC® HSS T3, 1.8 µparticle size, 2.1×100 mm
  Mobile phase A: Buffer/Acetonitrile=95/5 (v/v %)
  Mobile phase B: Buffer/Acetonitrile=5/95 (v/v %)

Buffer: 20 mM ammonium bicarbonate (adjusted to pH 7.0 using formic acid)
Flow rate: 0.4 mL/min
Column temperature: 40° C.
Wavelength: 285 nm
As such, the results of performing the compatibility test are shown in Table 12 below.

TABLE 12

|  | Maximum unknown impurity (%) | | | Total impurity (%) | | |
| --- | --- | --- | --- | --- | --- | --- |
|  | Initial | | | Initial | | |
|  | Before compression | After compression | 1 week | Before compression | After compression | 1 week |
| Mixture A | 0.14 | 0.13 | 0.13 | 0.4 | 0.5 | 0.4 |
| Mixture B | 0.14 | 0.30 | 0.29 | 0.4 | 0.8 | 0.7 |
| Mixture C | 0.13 | 0.14 | 0.19 | 0.4 | 0.5 | 0.5 |

As seen from the results of above Table 12, in the mixture of Lazertinib mesylate and magnesium stearate, no significant increase in the amount of impurity was observed both before and after compression and during storage for 1 week under a severe condition. However, in the mixture of Lazertinib mesylate and sodium stearyl fumarate, a significant increase in the amount of impurity was shown in the compressing process. Further, in the mixture of Lazertinib mesylate and colloidal silicon dioxide, a significant increase in the amount of impurity was shown for 1 week under a severe condition. Accordingly, it can be seen that the magnesium stearate has particularly excellent compatibility, with respect to Lazertinib mesylate.

Test Example 2. Dissolution Test (1) of Tablet

Figure 8:
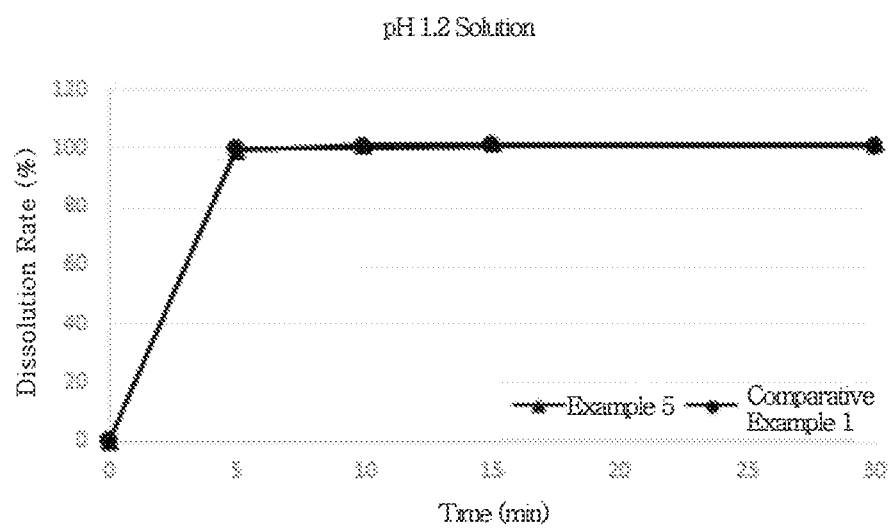
FIG. 8 illustrates results obtained by performing the dissolution test under a condition of pH 1.2 with respect to the tablet (Example 5) obtained according to the present disclosure and the tablet of Comparative Example (Comparative Example 1).
Figure 9:
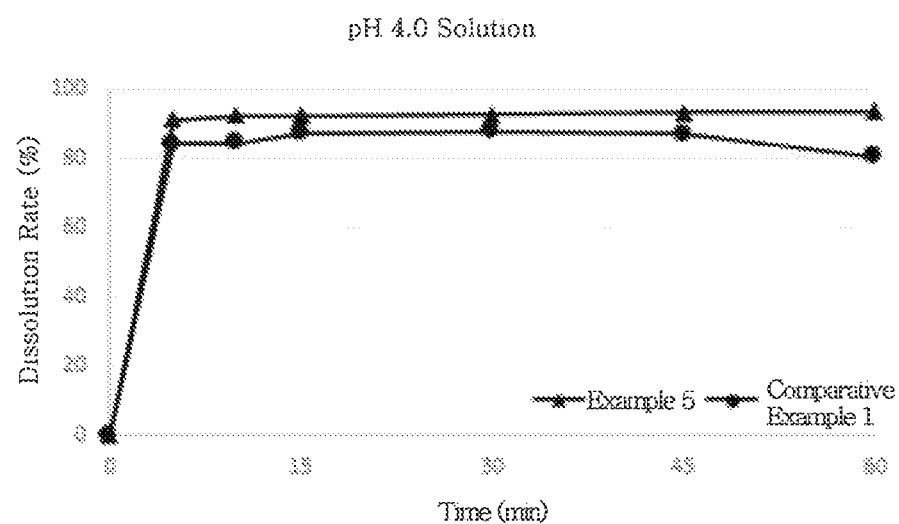
FIG. 9 illustrates results obtained by performing the dissolution test under a condition of pH 4.0 with respect to the tablet (Example 5) obtained according to the present disclosure and the tablet of Comparative Example (Comparative Example 1).
Figure 10:
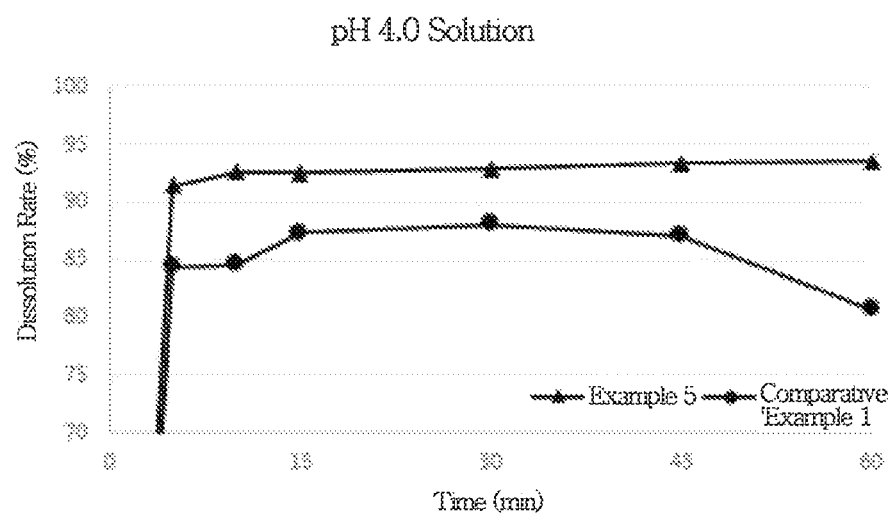
FIG. 10 illustrates an enlarged result of the dissolution test of FIG. 9.

A dissolution test was performed according to the following conditions with respect to the tablets of Example 5 and Comparative Example 1, and each sample was analyzed with HPLC.
<Conditions of Dissolution Test>
Dissolution Test Solution:
  1) pH 1.2 solution—First Solution of Disintegration Test of the Korean Pharmacopoeia
  2) pH 4.0 solution—acetate buffer solution (mixture of 0.05 mol/L acetic acid solution and 0.05 mol/L sodium acetate solution (41:9, v/v), and adjusted to pH 4.0)
    Amount of dissolution test solution: 900 mL
    Temperature of dissolution test solution: 37±0.5° C.
    Dissolution test method: Second method of Dissolution Test of the Korean Pharmacopoeia (50 rpm)
Sample Collection Time:
  1) pH 1.2 solution—5 minutes, 10 minutes, 15 minutes, 30 minutes
  2) pH 4.0 solution—5 minutes, 10 minutes, 15 minutes, 30 minutes, 45 minutes, 60 minutes
<HPLC Condition>
  Column: Luna C18 (2), 5 μm particle size, 4.6×50 mm
  Mobile phase: Buffer/Acetonitrile=40/60 (v/v %)
    Buffer: 20 mM ammonium bicarbonate (adjusted to pH 7.2 using formic acid)
  Flow rate: 2.0 mL/min
  Column temperature: 50° C.
  Wavelength: 298 nm
The results of the dissolution test performed as above are shown in FIGS. 8 to 9. In addition, an enlarged dissolution pattern of FIG. 9 is shown in FIG. 10. As illustrated in FIGS. 8 to 10, the tablet of Example 5 had no significant difference between the dissolution rate at pH 1.2 indicating a before-meal state and the dissolution rate at pH 4.0 indicating an after-meal state. On the contrary, in the tablet of Comparative Example 1, the dissolution rate at pH 4.0 was significantly reduced, compared to the dissolution rate at pH 1.2. Thus, the tablet of the present disclosure may minimize deviations in dissolution according to changes in pH according to food or drugs (e.g., antacids, etc.).

Test Example 3. Dissolution Test (2) of Tablet

Figure 11:
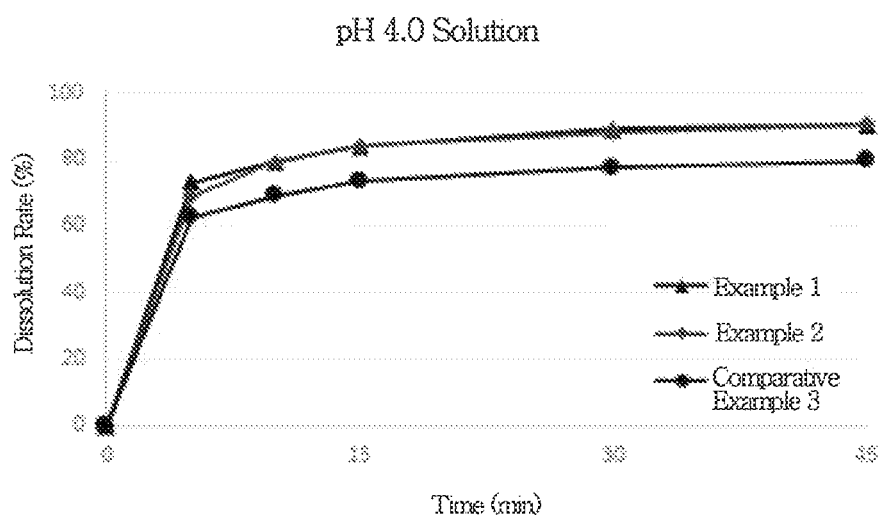
FIG. 11 illustrates results obtained by performing the dissolution test under a condition of pH 4.0 with respect to the tablets (Examples 1 and 2) obtained according to the present disclosure and the tablet of Comparative Example (Comparative Example 3).

A dissolution test was performed according to the following conditions with respect to the tablets of Examples 1 and 2 and Comparative Example 3, and each sample was analyzed with HPLC. HPLC analysis conditions are the same as those in Test Example 2.
<Conditions of Dissolution Test>
  Dissolution test solution: pH 4.0 solution—acetate buffer solution (mixture of 0.05 mol/L acetic acid solution and 0.05 mol/L sodium acetate solution (41:9, v/v), and adjusted to pH 4.0)
  Amount of dissolution test solution: 900 mL
  Temperature of dissolution test solution: 37±0.5° C.
  Dissolution test method: Second method of Dissolution Test of the Korean Pharmacopoeia (50 rpm)
  Sample collection time: 5 minutes, 10 minutes, 15 minutes, 30 minutes, 45 minutes, 60 minutes
The results of the dissolution test performed as above are shown in FIG. 11. As illustrated in FIG. 11, in the case of using a larger amount (about 3 times) of microcrystalline cellulose than mannitol, the dissolution rate at pH 4.0 was significantly reduced. On the contrary, it can be seen that the tablet of the present disclosure shows a uniform dissolution rate.

Test Example 4. Dissolution Test (3) of Tablet

A dissolution test was performed according to the following conditions with respect to the tablets of Example 7 and Comparative Examples 5 and 6, and each sample was analyzed with HPLC. HPLC analysis conditions are the same as those in Test Example 2.
<Conditions of Dissolution Test>
Dissolution Test Solution:
  1) Acid phase—0.1N hydrochloric acid solution 750 mL
  2) Buffer phase—1) acid phase 750 mL+0.2 M sodium triphosphate solution 250 mL
    Temperature of dissolution test solution: 37±0.5° C.
    Dissolution test method: Second method of Dissolution Test of the Korean Pharmacopoeia (50 rpm)
    (After performing a dissolution test for 30 minutes in the dissolution solution (750 mL) of an acid phase, 250 mL of a 0.2 M sodium triphosphate solution was added to become a dissolution solution (1,000 mL) of the buffer phase, and then the dissolution test was additionally performed for 60 minutes.)

Figure 12:
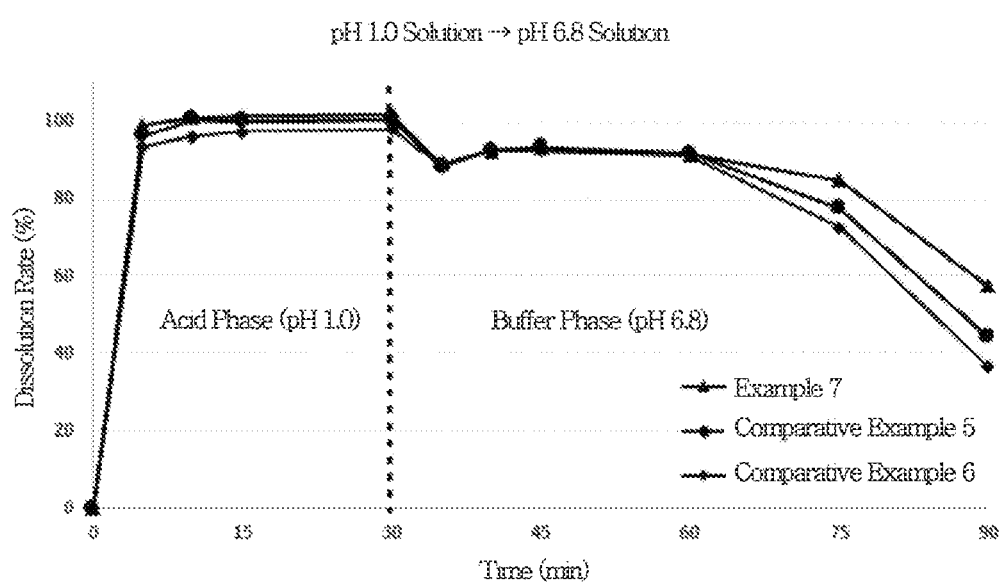
FIG. 12 illustrates results obtained by performing the dissolution test under the continuous condition of an acid phase (pH 1.0) and a buffer phase (pH 6.8) with respect to the tablet (Example 7) obtained according to the present disclosure and the tablets of Comparative Examples (Comparative Examples 5 and 6).

Sample Collection Time:
1) Acid phase—5 minutes, 10 minutes, 15 minutes, 30 minutes
2) Buffer phase—5 minutes, 10 minutes, 15 minutes, 30 minutes, 45 minutes, 60 minutes The results of the dissolution test performed as above are shown in FIG. 12. From the results of FIG. 12, it can be seen that in the tablet obtained using sodium croscarmellose as a disintegrating agent, precipitation of a drug in the buffer phase is most delayed.

Test Example 5. Stability Test

The tablets of Example 1 and Comparative Example 4 were put in an aluminum bag and stored for 2 weeks under a severe condition (60±2° C., 75±5% RH), and then the contents of a maximum unknown impurity and a total impurity were measured, respectively. The content of the impurity was analyzed by ultra performance liquid chromatography (UPLC). UPLC analysis conditions are the same as those in Test Example 1.

As such, the results of performing the stability test are shown in Table 13 below.

TABLE 13

| Sample | Maximum unknown impurity (%) | | | Total impurity (%) | | |
|---|---|---|---|---|---|---|
| | Initial | 1 week | 2 weeks | Initial | 1 week | 2 weeks |
| Example 1 | 0.01 | 0.04 | 0.05 | 0.4 | 0.3 | 0.4 |
| Comparative Example 4 | 0.01 | 0.10 | 0.10 | 0.4 | 0.4 | 0.4 |

As seen from the results of Table 13 above, in the tablet obtained according to the present disclosure, a significant increase in impurity was not observed. However, in the tablet of Comparative Example 4, the unknown impurity was significantly increased.

Test Example 6. Pharmacokinetic Test

With respect to the tablets of Example 7 and Comparative Example 2, pharmacokinetics in a beagle dog was compared with each other, respectively. The tablets (composition containing 80 mg as YH25448) prepared in Example 7 and Comparative Example 2 were orally administered to a beagle dog pre-fasting (fasting condition) for 14 hours the day before the test, and then a pharmacokinetic test was performed.

Figure 13:
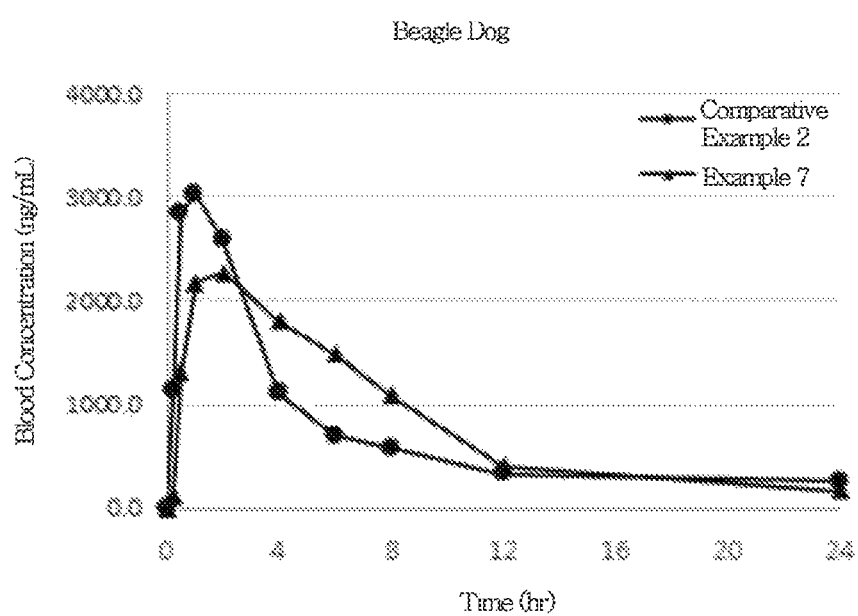
FIG. 13 illustrates a blood concentration profile obtained by performing a pharmacokinetic test with respect to the tablet (Example 7) obtained according to the present disclosure and the tablet of Comparative Example (Comparative Example 2).

A blood concentration profile obtained by performing the pharmacokinetic test as above is shown in FIG. 13. Further, pharmacokinetic parameters obtained from the blood concentration profile, that is, a maximum blood concentration ($C_{max}$) and an area under the blood concentration curve ($AUC_{last}$) are shown in Table 14 below.

TABLE 14

| | Example 7 | Comparative Example 2 |
|---|---|---|
| Maximum blood concentration ($C_{max}$, ng/ml) | 2353.0 | 3426.0 |
| Area under the blood concentration curve ($AUC_{last}$, ng · hr/mL) | 19657.8 | 17080.4 |

As results of Table 14 and FIG. 13, it can be seen that the tablet obtained according to the present disclosure has a high AUC value and excellent bioavailability. Further, the maximum blood concentration may be lowered, thereby being able to reduce the risk of toxicity.

What is claimed:

1. A pharmaceutical composition for oral administration comprising: a mesylate salt of N-(5-(4-(4-((dimethylamino)methyl)-3-phenyl-1H-pyrazol-1-yl) pirimidine-2-ylamino)-4-methoxy-2-morpholinophenyl) acrylamide (Lazertinib) as an active ingredient; and a combination of microcrystalline cellulose and mannitol as a diluent, wherein the combination is a dry blend of the microcrystalline cellulose and the mannitol in the absence of a solvent, and wherein N-(5-(4-(4-((dimethylamino)methyl-3-phenyl-1H-pyrazol-1-yl) pirimidine-2-ylamino)-4-methoxy-2-morpholinophenyl) acrylamide mesylate is a crystalline form having a PXRD pattern with peaks at 5.614, 17.143, and 21.585°2θ±0.2°2θ.

2. The pharmaceutical composition of claim 1, wherein a weight ratio of the microcrystalline cellulose to the mannitol is in a range of 1:0.5 to 1:3.

3. The pharmaceutical composition of claim 1, wherein a weight ratio of the microcrystalline cellulose to the mannitol is in a range of 1:0.9 to 1:3.

4. The pharmaceutical composition of claim 1, wherein a weight ratio of the microcrystalline cellulose to the mannitol is in a range of 1:0.9 to 1:1.5.

5. The pharmaceutical composition of claim 1, further comprising: croscarmellose sodium as a disintegrating agent.

6. The pharmaceutical composition of claim 5, wherein the croscarmellose sodium exists in a range of 2 to 5 wt %, with respect to the total weight of the composition.

7. The pharmaceutical composition of claim 1, further comprising: magnesium stearate as a lubricant.

8. The pharmaceutical composition of claim 1, further comprising croscarmellose sodium as a disintegrating agent; and magnesium stearate as a lubricant.

9. The pharmaceutical composition of claim 1, wherein the pharmaceutical composition comprises 5 to 54 wt % of N-(5-(4-(4-((dimethylamino)methyl)-3-phenyl-1H-pyrazol-1-yl) pirimidine-2-ylamino)-4-methoxy-2-morpholinophenyl) acrylamide mesylate; 45 to 87 wt % of the combination of microcrystalline cellulose and mannitol; 0.5 to 10 wt % of croscarmellose sodium; and 0.4 to 2 wt % of magnesium stearate.

10. The pharmaceutical composition of claim 1, wherein the pharmaceutical composition comprises 7 to 46 wt % of N-(5-(4-(4-((dimethylamino)methyl)-3-phenyl-1H-pyrazol-1-yl) pirimidine-2-ylamino)-4-methoxy-2-morpholinophenyl) acrylamide mesylate; 50 to 87 wt % of the combination of microcrystalline cellulose and mannitol; 2 to 5 wt % of croscarmellose sodium; and 0.5 to 1.5 wt % of magnesium stearate.

11. The pharmaceutical composition of claim 1, wherein N-(5-(4-(4-((dimethylamino)methyl-3-phenyl-1H-pyrazol-1-yl) pirimidine-2-ylamino)-4-methoxy-2-morpholinophenyl) acrylamide mesylate is a crystalline form having a PXRD pattern with peaks at 5.614, 12.394, 14.086, 17.143, 18.020, 19.104, 21.585, 22.131, and 22.487°2θ±0.2° 2θ.

12. The pharmaceutical composition of claim 1, wherein N-(5-(4-(4-((dimethylamino)methyl)-3-phenyl-1H-pyrazol-1-yl) pirimidine-2-ylamino)-4-methoxy-2-morpholinophenyl) acrylamide mesylate is a crystalline form having a differential scanning calorimeter (DSC) thermogram with an endothermic peak at 210 to 230° C.

13. The pharmaceutical composition of claim 12, wherein N-(5-(4-(4-((dimethylamino)methyl-3-phenyl-1H-pyrazol-1-yl) pirimidine-2-ylamino)-4-methoxy-2-morpholinophenyl) acrylamide mesylate is a crystalline form having a differential scanning calorimeter (DSC) thermogram with an endothermic peak at 217±2° C.

14. A pharmaceutical composition for oral administration comprising a dry blend of: N-(5-(4-(4-((dimethylamino)methyl)-3-phenyl-1H-pyrazol-1-yl)pirimidene-2-ylamino)-4-methoxy-2-morpholinophenyl) acrylamide mesylate as an active ingredient; and a combination of microcrystalline cellulose and mannitol as a diluent, wherein the pharmaceutical composition comprises of 5 to 54 wt % of N-(5-(4-(4-((dimethylamino)methyl-3-phenyl-1H-pyrazol-1-yl)pirimidine-2-ylamino)-4-methoxy-2-morpholinophenyl) acrylamide mesylate; 45 to 87 wt % of the combination of microcrystalline cellulose and mannitol, and wherein N-(5-(4-(4-((dimethylamino)methyl-3-phenyl-1H-pyrazol-1-yl) pirimidine-2-ylamino)-4-methoxy-2-morpholinophenyl) acrylamide mesylate is a crystalline form having a PXRD pattern with peaks at 5.614, 17.143, and 21.585°2θ±0.2° 2θ.

15. The pharmaceutical composition of claim 14, wherein the pharmaceutical composition comprises of 5 to 25 wt % of N-(5-(4-(4-((dimethylamino)methyl)-3-phenyl-1H-pyrazol-1-yl) pirimidine-2-ylamino)-4-methoxy-2-morpholinophenyl) acrylamide mesylate.

16. The pharmaceutical composition of claim 15, wherein N-(5-(4-(4-((dimethylamino)methyl)-3-phenyl-1H-pyrazol-1-yl) pirimidine-2-ylamino)-4-methoxy-2-morpholinophenyl) acrylamide mesylate is a crystalline form having a PXRD pattern with peaks at 5.614, 12.394, 14.086, 17.143, 18.020, 19.104, 21.585, 22.131, and 22.487°2θ±0.2° 2θ.

17. The pharmaceutical composition of claim 15, wherein N-(5-(4-(4-((dimethylamino)methyl)-3-phenyl-1H-pyrazol-1-yl) pirimidine-2-ylamino)-4-methoxy-2-morpholinophenyl) acrylamide mesylate is a crystalline form having a differential scanning calorimeter (DSC) thermogram with an endothermic peak at 217±2° C.

18. A pharmaceutical composition for oral administration comprising: a mesylate salt of N-(5-(4-(4-((dimethylamino)methyl)-3-phenyl-1H-pyrazol-1-yl) pirimidine-2-ylamino)-4-methoxy-2-morpholinophenyl) acrylamide (Lazertinib) as an active ingredient; and a combination of microcrystalline cellulose and mannitol as a diluent, wherein the combination is a dry blend of the microcrystalline cellulose and the mannitol in the absence of a solvent, and wherein N-(5-(4-(4-((dimethylamino)methyl-3-phenyl-1H-pyrazol-1-yl) pirimidine-2-ylamino)-4-methoxy-2-morpholinophenyl) acrylamide mesylate is a crystalline form having a differential scanning calorimeter (DSC) thermogram with an endothermic peak at 217±2° C.

* * * * *

UNITED STATES PATENT AND TRADEMARK OFFICE
CERTIFICATE OF CORRECTION

| | |
|---|---|
| PATENT NO. | : 12,318,390 B2 |
| APPLICATION NO. | : 17/285161 |
| DATED | : June 3, 2025 |
| INVENTOR(S) | : Seongkyu Kim et al. |

It is certified that error appears in the above-identified patent and that said Letters Patent is hereby corrected as shown below:

On the Title Page

Item (56) Under Column no. 2, Line no. 3, Replace:
"BioImpacts:"
With:
--BioImpacts:--

In the Claims

Under Column no. 18, Claim 1, Line no. 10, Replace:
"yl) pirimidine"
With:
--yl)pirimidine--

Under Column no. 18, Claim 1, Line no. 11, Replace:
"morpholinophenyl) acrylamide"
With:
--morpholinophenyl)acrylamide--

Under Column no. 18, Claim 1, Line nos. 16-17, Replace:
"yl) pirimidine"
With:
--yl)pirimidine--

Under Column no. 18, Claim 1, Line nos. 17-18, Replace:
"morpholinophenyl) acrylamide"
With:
--morpholinophenyl)acrylamide--

Signed and Sealed this
Fourteenth Day of October, 2025

John A. Squires
*Director of the United States Patent and Trademark Office*

CERTIFICATE OF CORRECTION (continued)
U.S. Pat. No. 12,318,390 B2

Under Column no. 18, Claim 9, Line no. 43, Replace:
"yl) pirimidine"
With:
--yl)pirimidine--

Under Column no. 18, Claim 9, Line nos. 43-44, Replace:
"morpholinophenyl) acrylamide"
With:
--morpholinophenyl)acrylamide--

Under Column no. 18, Claim 10, Line no. 51, Replace:
"yl) pirimidine"
With:
--yl)pirimidine--

Under Column no. 18, Claim 10, Line nos. 51-52, Replace:
"morpholinophenyl) acrylamide"
With:
--morpholinophenyl)acrylamide--

Under Column no. 18, Claim 11, Line no. 58, Replace:
"yl) pirimidine"
With:
--yl)pirimidine--

Under Column no. 18, Claim 11, Line nos. 58-59, Replace:
"morpholinophenyl) acrylamide"
With:
--morpholinophenyl)acrylamide--

Under Column no. 18, Claim 12, Line no. 64, Replace:
"yl) pirimidine"
With:
--yl)pirimidine--

Under Column no. 18, Claim 12, Line nos. 64-65, Replace:
"morpholinophenyl) acrylamide"
With:
--morpholinophenyl)acrylamide--

Under Column no. 19, Claim 13, Line no. 3, Replace:
"yl) pirimidine"
With:
--yl)pirimidine--

CERTIFICATE OF CORRECTION (continued)
U.S. Pat. No. 12,318,390 B2

Under Column no. 19, Claim 13, Line nos. 3-4, Replace:
"morpholinophenyl) acrylamide"
With:
--morpholinophenyl)acrylamide--

Under Column no. 19, Claim 14, Line no. 10, Replace:
"morpholinophenyl) acrylamide"
With:
--morpholinophenyl)acrylamide--

Under Column no. 19, Claim 14, Line nos. 18-19, Replace:
"yl) pirimidine"
With:
--yl)pirimidine--

Under Column no. 19, Claim 14, Line nos. 19-20, Replace:
"morpholinophenyl) acrylamide"
With:
--morpholinophenyl)acrylamide--

Under Column no. 19, Claim 15, Line no. 25, Replace:
"yl) pirimidine"
With:
--yl)pirimidine--

Under Column no. 19, Claim 15, Line nos. 25-26, Replace:
"morpholinophenyl) acrylamide"
With:
--morpholinophenyl)acrylamide--

Under Column no. 20, Claim 16, Line no. 3, Replace:
"yl) pirimidine"
With:
--yl)pirimidine--

Under Column no. 20, Claim 16, Line nos. 3-4, Replace:
"morpholinophenyl) acrylamide"
With:
--morpholinophenyl)acrylamide--

Under Column no. 20, Claim 17, Line no. 9, Replace:
"yl) pirimidine"
With:
--yl)pirimidine--

CERTIFICATE OF CORRECTION (continued)
U.S. Pat. No. 12,318,390 B2

Under Column no. 20, Claim 17, Line nos. 9-10, Replace:
"morpholinophenyl) acrylamide"
With:
--morpholinophenyl)acrylamide--

Under Column no. 20, Claim 18, Line no. 15, Replace:
"yl) pirimidine"
With:
--yl)pirimidine--

Under Column no. 20, Claim 18, Line nos. 15-16, Replace:
"morpholinophenyl) acrylamide"
With:
--morpholinophenyl)acrylamide--

Under Column no. 20, Claim 18, Line nos. 21-22, Replace:
"yl) pirimidine"
With:
--yl)pirimidine--

Under Column no. 20, Claim 18, Line nos. 22-23, Replace:
"morpholinophenyl) acrylamide"
With:
--morpholinophenyl)acrylamide--